United States Patent [19]
Fildes et al.

[11] Patent Number: 5,643,724
[45] Date of Patent: Jul. 1, 1997

[54] METHODS AND REAGENTS FOR GLYCOPHORIN A TYPING

[75] Inventors: Nicola Jane Fildes, Walnut Creek; Rebecca Lynne Reynolds, Alameda, both of Calif.

[73] Assignee: Roche Molecular Systems, Inc., Branchburg, N.J.

[21] Appl. No.: 255,264

[22] Filed: Jun. 6, 1994

[51] Int. Cl.$^6$ ............... C12Q 1/68; C12P 19/34
[52] U.S. Cl. ............... 435/6; 435/91.2
[58] Field of Search ............ 435/6, 91.2; 536/23.5, 536/24.33; 535/24.35

[56] References Cited

U.S. PATENT DOCUMENTS 4,683,195  7/1987  Mullis et al. ............... 435/6

OTHER PUBLICATIONS

Furthmayr, Feb., 1978, "Structural Comparison of Glycophorins and Immunochemical Analysis of Genetic Variants" Nature 271:519–524.

Siebert and Fukuda, Oct., 1987, "Molecular Cloning of a Human Glycophorin B cDNA: Nucleotide Sequence and Genomic Relationship to Glycophorin A" Proc. Natl. Acad. Sci. USA 84:6735–6739.

Kudo and Fukuda, Jun., 1989, "Structural Organization of Glycophorin A and B Genes: Glycophorin B Gene Evolved by Homologous Recombination at Alu Repeat Sequences" Proc. Natl. Acad. Sci. USA 86:4619–4623.

Fildes et al., 1994, American Academy Forensic Sciences (46th Annual Meeting) p. 97, Abstract No. B110 "Discovery of a New GYPA Allele in the U.S. African American Population".

Huang et al J. Biol. Chem 267:3336–3342 (1992).

*Primary Examiner*—Eggerton A. Campbell
*Attorney, Agent, or Firm*—George W. Johnston; Stacey R. Sias; Douglas A. Petry

[57] ABSTRACT

Methods and reagents for determining an individual's genotype at the Glycophorin A locus with respect to a set of five alleles using sequence-specific oligonucleotide probes enable one to type samples from a variety of sources, including samples comprising RNA or cDNA templates, and can be applied to nucleic acids in which a target region spanning the polymorphism has been amplified. This typing facilitates typing tissue for determining individual identity and has application in the field of forensic science.

21 Claims, No Drawings

5,643,724

1

METHODS AND REAGENTS FOR GLYCOPHORIN A TYPING

BACKGROUND OF THE INVENTION

1. Field of the Invention

The present invention relates to the field of molecular biology and nucleic acid chemistry. More specifically, it relates to methods and reagents genotyping at the Glycophorin A locus.

2. Description of Related Art

Glycophorin A (GYPA) is one of the major sialoglycoproteins of the hyman erythrocyte membrane. Glycophorin A carries the M or N blood group antigen, which is determined by the amino acids at residues 1 and 5. A structural comparison of glycophorin proteins and an immunochemical analysis of genetic variants is described in Furthmayr, 1978, *Nature* 271:519-524.

Glycophorin A is encoded by a gene on human chromosome 4 which consist of 7 exons. The structural organization of the Glycophorin A gene is described in Kudo and Fukuda, 1989, *Proc. Natl. Acad. Sci. USA* 86:4619-4623, incorporated herein by reference. The nucleotide sequences of the Glycophorin A alleles that encode the proteins that carry the M and N blood group antigens are reported in Siebert and Fukuda, 1987, *Proc. Natl. Acad. Sci. USA* 84:6735-6739.

The invention of the polymerase chain reaction (PCR), a method for amplifying specific sequences of nucleic acids, makes possible the rapid demotion of nucleic acids present in a sample in what was previously an undetectably low quantity (see U.S. Pat. Nos. 4,683,195; 4,683,202; and 4,965,188, each of which is incorporated herein by reference). Direct detection of an amplified nucleic acid sequence by hybridization with a sequence-specific oligonucleotide probe makes possible the detection of single nucleotide changes in sequence. The detection of allelic nucleotide sequence variations by hybridization of amplified gene nucleic acid sequences with allele-specific nucleic acid probes is described in Saiki et al., 1986, *Nature* 324:163-166.

One application of genetic typing is the identification of individuals. The use of PCR amplification and nucleic acid probes has revolutionized the field of forensic serology (see Reynolds and Sensabaugh 1991, *Anal. Chem.* 63:2-15). With PCR and other nucleic acid amplification methods, DNA typing can now be done with samples that contain insufficient DNA for typing by any other means. For example, single hairs provide enough DNA for PCR-based DNA typing. (Higuchi et al., 1988, *Nature* 332:543-546).

The discriminative power of a DNA genotyping assay depends on the number and frequency of alleles found at a locus. The discovered of additional alleles along with sequence specific probes capable of detecting the alleles at the Glycophorin A locus would substantially improve the discriminative power of a Glycophorin A DNA typing assay and thereby improve its utility in forensic methodology.

SUMMARY OF THE INVENTION

The present invention provides methods and reagents for determining an individual's genotype at the Glycophorin A locus.

One aspect of the invention relates to the nucleotide sequences of newly discovered alleles at the Glycophorin A locus. Only two common alleles have been described in the prior art, corresponding to the two serological blood group types. Two additional alleles, as defined by the variant nucleic acid sequence within the detected region specified herein, have been found which subdivide the class of alleles which encode the protein carrying the M blood group antigen. An additional allele has been found that subdivides the class of alleles which encode the protein carrying the N blood group antigen.

One aspect of the invention relates to a process for determining an individual's genotype at the Glycophorin A locus from a sample containing nucleic acid obtained from the individual. The process comprises hybridizing the sample nucleic acid with a panel of sequence-specific oligonucleotide (SSO) probes; each of the probes is complementary to one of the variant nucleotide sequences of the Glycophorin A alleles. Hybridization is carried out under conditions such that the SSO probes bind to the nucleic acid to form stable hybrid duplexes only if the hybridizing region of each of the probes is exactly complementary to the nucleic acid. The hybrids formed between the nucleic acid and the SSO probes can then be detected.

In a preferred embodiment of the invention, the sample contains amplified nucleic acids. Any of the known methods for increasing the copy number of a region of nucleic acid in vitro can be used to amplify the nucleic acid, so long as the relevant region of nucleic acid is amplified. PCR is the preferred amplification method.

Another aspect of the invention relates to SSO probes useful for discriminating between the Glycophorin A alleles, both the newly discovered and previously known, that may be present in the sample.

Another aspect of the invention relates to kits useful for determining the Glycophorin A genotype of an individual. These kits take a variety of forms and comprise one or more SSO probes and, in one embodiment, comprise a panel of probes sufficient to determine the Glycophorin A genotype. The kits can also comprise one or more amplification reagents, e.g., primers, polymerase, buffers, and nucleoside triphosphates.

Another aspect of the invention relates to forensic methods to determine the probable origin of a biological sample. The discovery of additional alleles substantially improves the discriminative power of Glycophorin A DNA typing methodology and will have an important impact on forensic methodology.

DETAILED DESCRIPTION OF THE INVENTION

To aid in understanding the invention, several terms are defined below.

The terms "Glycophorin A" gene and "Glycophorin A" locus refer to a transcribed region of DNA that contains the coding sequence for the Glycophorin A proteins and the untranslated intervening sequences.

The term "alleles" refers to variants of the nucleotide sequence of a gene. An allele is defined by the presence of a specific subsequence, which may not include the entire gene. Hence, an allele may consist of a set of sequence variants, all of which contain the specific subsequence that defines the allele, wherein the sequence variation is outside of the defining region.

The term "variant sequence that defines an allele", as used herein, refers to a subsequence of a Glycophorin A nucleic acid sequence that includes a variant sequence that is unique to the allele defined.

A variant sequence is said to distinguish a first allele from a second allele if the variant sequence is contained in the first allele and not contained in the second allele.

The term "allele A", as used herein, refers to sequence variants of the Glycophorin A gene that contain the sequence provided in SEQ ID NO: 1. Allele A designates the allele reported to encode the protein that carries the M blood group antigen (see Siebert and Fukuda, 1987, Supra). The term "allele B", as used herein, refers to sequence variants of the Glycophorin A gene that contain the sequence variation provided in SEQ ID NO: 2. Allele B designates the allele reported to encode the protein that carries the N blood group antigen (see Siebert and Fukuda, 1987, supra). Similarly, allele A', allele A", and allele B' refer to the sequence variants of the Glycophorin A gene that contain the sequences provided in SEQ ID NOS. 3, 4, and 5, respectively.

The term "genotype" refers to a description of the alleles of a gene contained in an individual or a sample.

The terms "polymorphic" and "polymorphism", as used herein, refer to the condition in which two or more variants of a specific DNA sequence can be found in a population.

The terms "polymorphic gene" and "polymorphic region" refer to that region of the DNA where a polymorphism occurs.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, was well as double- and single-stranded RNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–15 1; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference.

The term "hybridization" refers the formation of a duplex structure by two single stranded nucleic acids due to complementary base pairing. Hybridization can occur between complementary nucleic acid strands or between nucleic acid strands that contain minor regions of mismatch. Conditions under which only fully complementary nucleic acid strands will hybridize are referred to as "stringent hybridization conditions". Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs.

The term "probe" refers to a oligonucleotide which forms a duplex structure with a sequence of a target nucleic acid due to complementary base pairing. The probe will consist of 10 to 50 nucleotides, more preferably from 15 to 40 nucleotides, corresponding to a region of the target sequence. "Corresponding" means identical to or complementary to the designated nucleic acid. An oligonucleotide probe can be bound to additional features which allow for the detection or immobilization of the probe but do not alter the hybridization characteristics of the hybridizing region.

The terms "sequence-specific oligonucleotide" and "SSO" refer to oligonucleotide probes wherein the hybridizing region is exactly (i.e., fully) complementary to the sequence to be detected. The use of stringent hybridization conditions, which are conditions under which a probe will hybridize only to the exactly complementary target sequence, allows the detection of the specific target sequence. Stringent hybridization conditions are well known in the art (see, e.g., Sambrook et al., 1985, *Molecular Cloning—A Laboratory Manual*, Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Typically, stringent conditions will be those in which the salt concentration is at least about 0.2 molar at pH 7 and the temperature is at least about 50° C. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis.

The term "target region" refers to a region of a nucleic acid which is to be analyzed and usually includes a polymorphic region.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. A purified thermostable polymerase enzyme is described more fully in U.S. Pat. No. 4,889,818, incorporated herein by reference, and is commercially available from Perkin-Elmer, Norwalk, Conn.

The present invention provides methods and reagents for determining the Glycophorin A genotype of an individual. In part, the invention results from the discovery of previously unknown Glycophorin A alleles. The sequence of the A and B alleles of the Glycophorin A gene are provided in Siebert and Fukuda, 1987, Supra. Three additional alleles have been discovered, designated A', A", and B'. The A' and A" alleles subdivide the class of alleles that encode a protein that carries the M blood group antigen. The B' allele subdivides the class of alleles that encode a protein that carries the N blood group antigen. The nucleotide sequences of the alleles are provided in Table 1.

The nucleotide sequence of a region of each of the alleles is provided in Table 1, below, shown below, 5' to 3'. Each sequence corresponds to the region of the Glycophorin A gene between the hybridization sites of the two amplification primers described below. In each sequence, the nucleotide bases that differ from the A allele sequence are shown underlined. The variant sequences that define the A, A', A", B, or B' allele are those subsequences of the sequences provided in Table 1 that contain a sequence variation that distinguishes the allele, and can be determined by comparing the sequences provided in Table 1.

Table 1

Glycophorin A Allele Sequences

Allele A (SEQ ID NO: 1)
ATATGCTTTA TGGTCCGCTC AGTCACCTCG TTCT-
TAATCC CTTTCTCAAC TTCTATGTTA
TACAGCAATT GTGAGCATAT CAGCATCAAG TAC-
CACTGGT GTGGCAATGC ACACTTCAAC
CTCTTCTTCA GTCACAAAGA
Allele A' (SEQ ID NO: 2)
ATATGCTTTA TGGTCTGCTC AGTCACCTCG TTCT-
TAATCC CTTTCTCAAC TTCTATTTTA
TACAGAAATT GTGAGCATAT CAGCATGGAG
TACCTCTGGT GTGGCAATGC ACACTTCAAC
CTCCTCTTCG GTCACAAAGA
Allele A" (SEQ ID NO: 3)
ATATGCTTTA TGGTCTGCTC AGTCACCTCG TTCT-
TAATCC CTTTCTCAAC TTCTATTTTA
CACAGAAATT GTGAGCATAT CAGCATGGAG
TACCTCTGGT GTGGCAATGC ACACTTCAAC
CTCCTCTTCG GTCACAAAGA
Allele B (SEQ ID NO: 4)
ATATGCTTTA TGGTCCGCTC AGTCACCTCG TTCT-
TAATCC CTTTCTCAAC TTCTATTTTA
TACAGCAATT GTGAGCATAT CAGCATTAAG TAC-
CACTGAG GTGGCAATGC ACACTTCAAC
CTCTTCTTCA GTCACAAAGA
Allele B' (SEQ ID NO: 5)
ATATGCTTTA TGGTCCGCTC AGTCACCTCG TTCT-
TAATCC CTTTCTCAAC TTCTATTTTA
TACAGAAATT GTGAGCATAT CAGCATTAAG TAC-
CACTGAG GTGGCAATGC ACACTTCAAC
TTCTTCTTCA GTCACAAAGA The alleles can be detected and distinguished using sequence-specific oligonucleotide probes. Suitable stringent hybridization conditions, which will depend on the exact size of the probe and placement of the target region to which the probe hybridizes, can be selected empirically using the guidance provided in the prior art. The probes need not hybridize to the entire region shown above. Probes need only to hybridize to a subregion that contains variant sequence that defines an allele or that contains a variant sequence that distinguishes a specific allele. Suitable subregions are those that contain the nucleotide variation shown underlined in Table 1. Similarly, one of skill in the art will recognize that probes for detecting all the alleles can be designed by selecting target regions in which no sequence variation occurs. Such regions also are determined by comparing the sequences provided in Table 1.

The DNA sequences provided above are an important aspect of the present invention. Although only one strand of the sequence is shown, those of skill in the art will recognize that the complementary strand of each sequence can be inferred from the information depicted above. This information enables the construction of probes of the invention in addition to the exemplified probes.

A preferred set of sequence-specific probes for distinguishing alleles A, A', A", B, and B' is provided in Table 2, below. Each of the probes shown in Table 2 additionally has a 100 base poly-T tail attached to the 5' end to enable immobilization on a nylon membrane. MAG36 (SEQ ID NO: 8) hybridizes to both the A' and A" alleles and distinguishes these alleles from the A allele. The A' and A" alleles can then be distinguished using the A"-specific probe (SEQ ID NO: 9). Similarly, MAG31 (SEQ ID NO: 7) hybridizes to both the B and B' alleles and distinguishes these alleles from the A, A', and A" alleles. The B and B' alleles can be distinguished using the B'-specific probe (SEQ ID NO: 10). The A"- and B'-specific probes hybridize to variant sequences that define the A" and B' alleles, i.e., variant sequences that are unique to the A" and B' alleles.

TABLE 2

| Probe | Allele | Seq. ID No. | Sequence |
|---|---|---|---|
| | | Allele Specific Probes | |
| MAG09 | A | 6 | 5'-CATTGCCACACCAGTGGTAC |
| MAG31 | B, B' | 7 | 5'-GTACCACTGAGGTGGCAATGATT |
| MAG36 | A', A" | 8 | 5'-CATTGCCACACCAGAGGTAC |
| A"-probe | A" | 9 | 5'-CTTCTATTTTACACAGAAATTGT |
| B'-probe | B' | 10 | 5'-CTGAAGAAGAAGTTGAAGTGT |

Each probe is designed as a subsequence of the target allele sequence of suitable size and placement. One of skill in the art will realize that, for detecting double-stranded target DNA, the complement of each suitable sequence-specific probe is also a suitable sequence-specific probe.

In a preferred embodiment of the invention, the process for determining the Glycophorin A genotype comprises amplifying a nucleic acid sequence which contains the variable portion of a Glycophorin A gene, determining the variant Glycophorin A allele sequence present using SSO probes; and inferring the Glycophorin A genotype from the pattern of binding of the SSO probes to the amplified target sequence. Preferred primers for the PCR amplification of the Glycophorin A target region are listed in Table 3. These primers amplify a 190 base-pair (bp) fragment (consisting of the 140 bp region shown in Table 1 plus the two flanking 25 bp primer hybridization regions).

TABLE 3

Glycophorin A Amplification Primers

| Primer | Seq. ID No. | Sequence |
| --- | --- | --- |
| RS362 | 11 | 5'-GGATGTGAGGAATTTGTCTTTTGCA |
| RS364 | 12 | 5'-CCATTTGTCTGTGATGAGATGTAAC |

Any type of tissue containing Glycophorin A nucleic acid may be used for determining the Glycophorin A genotype of an individual. Simple and rapid methods of preparing samples for PCR are described in Higuchi, 1989, in *PCR Technology* (Erlich ed., Stockton Press, New York). Because the genotyping methods of the present invention can utilize amplified nucleic acids, and because the PCR technique can amplify extremely small quantities of nucleic acid, the Glycophorin A genotype can be determined even from samples containing only a few copies of the Glycophorin A gene. For instance, even a single hair contains enough DNA for purposes of the present invention, as evidenced by the DQα DNA typing methods described by Higuchi et al., 1988, supra. The feasibility of using single sperm for DNA typing is demonstrated in Li et al., 1988, *Nature* 335:441–417.

In general, the nucleic acid in the sample will be DNA, most usually genomic DNA. However, the present invention can also be practiced with other nucleic acids, such as messenger RNA or cloned DNA, and the nucleic acid may be either single-stranded or double-stranded in the sample and still be suitable for purposes of the present invention. Those skilled in the art recognize that whatever the nature of the nucleic acid, the nucleic acid can be typed by the present method merely by taking appropriate steps at the relevant stage of the process. If PCR is used to amplify the nucleic acid in the sample, then the sample will usually comprise double-stranded DNA after amplification and before probe hybridization.

The polymerase chain reaction (PCR) amplification process is well known in the art and described in U.S. Pat. Nos. 4,683,195; 4,683,202; and 4,965,188, each incorporated herein by reference. Commercial vendors, such as Perkin Elmer, Norwalk, Conn., market PCR reagents and publish PCR protocols. For ease of understanding the advantages provided by the present invention, a summary of PCR is provided.

In each cycle of a PCR amplification, a double-stranded target sequence is denatured, primers are annealed to each strand of the denatured target, and the primers are extended by the action of a DNA polymerase. The process is repeated typically between 25 and 40 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

Due to the enormous amplification possible with the PCR process, small levels of DNA carryover from samples with high DNA levels, positive control templates, or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, *Nature* 339:237–238, and Kwok and Orrego, in: Innis et al. eds., 1990 *PCR Protocols: A Guide to Methods and Applications*, Academic Press, Inc., San Diego, Calif., which are incorporated herein by reference.

Enzymatic methods to reduce the problem of contamination of a PCR by the amplified nucleic acid from previous reactions are described in PCT patent publication U.S. Ser. No. 91/05210 and U.S. Pat. No. 5,035,996, both incorporated herein by reference. The methods allow the enzymatic degradation of any amplified DNA from previous reactions. PCR amplifications are carried out in the presence of dUTP instead of dTTP. The resulting double-stranded amplification product which incorporates uracil is subject to degradation by uracil-N-glycosylase (UNG), whereas normal thymine-containing DNA is not degraded by UNG. Amplification reaction mixture are treated with UNG before amplification to degrade all uracil containing DNA that could serve as target. Because the only source of uracil-containing DNA is the amplified product of a previous reaction, this method effectively eliminates the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-inactivated environment and are not degraded.

Although the polymerase chain reaction is the preferred amplification method, amplification of target sequences in a sample may be accomplished by any known method, such as ligase chain reaction (Wu and Wallace 1988, *Genomics* 4:560–569, incorporated herein by reference), the TAS amplification system (Kwoh et al., 1989, *Proc. Natl. Acad. Sci. USA* 86:1173–1177, incorporated herein by reference), and self-sustained sequence replication (Guatelli et al., 1990, *Proc. Natl. Acad. Sci. USA* 87:1874–1878, incorporated herein by reference), each of which provides sufficient amplification so that the target sequence can be detected by nucleic acid hybridization to an SSO probe. Alternatively, methods that amplify the probe to detectable levels can be used, such as Qβ-replicase amplification (Kramer and Lizardi, 1989, *Nature* 339:401–402, and Lomeli et al., 1989, *Clin. Chem.* 35:1826–1831, both of which are incorporated herein by reference). A review of known amplification methods is provided in Abramson and Myers, 1993, *Current Opinion in Biotechnology* 4:41–47, incorporated herein by reference. The term "probe", as used herein, encompasses the sequence-specific oligonucleotides used in the above procedures; for instance, the two or more oligonucleotides used in LCR are "probes" for purposes of the present invention, even though some embodiments of LCR only require ligation of the probes to indicate the presence of an allele.

Following amplification of a region of the Glycophorin A gene, the Glycophorin A genotype of an individual can be determined by any means which discriminates the sequence variations found in the amplified fragments. For example, changes in the mobility measured by gel electrophoresis can be used to distinguish the allelic sequences. A preferred detection protocol involves hybridization to sequence-specific probes. The sequence-specific oligonucleotide probes of the present invention are designed to be complementary to one of the particular variant sequences which define the Glycophorin A alleles. The SSO probes, when used under stringent hybridization conditions wherein probes hybridize only to exactly complementary sequences, enable the detection and discrimination of the Glycophorin A alleles. If sufficient nucleic acid is present in the sample, detection by probe hybridization may be carried out without prior amplification of the target sequence.

The assay methods for detecting hybrids formed between SSO probes and target nucleic acid sequences can require that the probes be bound to additional features to permit detection or to facilitate immobilization of the probe. Such additional features bound to the probes to allow detection or immobilization should not affect the hybridization properties of the probes which enable the detection and discrimination of Glycophorin A alleles.

Probes can be labeled by binding to a label detectable by spectroscopic, photochemical, biochemical, immunochemical, or chemical means. Useful labels include $^{32}P$, fluorescent dyes, electron-dense reagents, enzymes (as commonly used in ELISAS), biotin, or haptens and proteins for which antisera or monoclonal antibodies are available.

Labeled probes of the invention can be synthesized and labeled using the techniques described above for synthesizing oligonucleotides. For example, the probe may be labeled at the 5'-end with $^{32}P$ by incubating the probe with $^{32}P$-ATP and kinase. A suitable non-radioactive label for SSO probes is horseradish peroxidase (HRP). Methods for preparing and detecting probes containing this label are described in the Examples, below, and in U.S. Pat. Nos. 4,914,210, and 4,962,029; both incorporated herein by reference. The use of such labeled probes is also described in U.S. Pat. No. 4,789,630; Saiki et al., 1988, *N. Eng. J. Med.* 319:537–541; and Bugawan et al., 1988, *Bio/Technology* 6:943–947, each of which is incorporated herein by reference. Useful chromogens for the detection of HRP labeled probes include red leuco dye and 3,3', 5,5'-tetramethylbenzidine (TMB).

Examples of additional features that are bound to the probes to allow immobilization of the probes include a long poly-dT "tail" that can be fixed to a nylon support by irradiation, a technique described in more detail in PCT Patent Publication No. WO 89/11548, incorporated herein by reference. For example, the probes shown in Table 1, above, can be bound to 100 nucleotide poly-T tails which are then used to immobilize the probes.

The probes of the invention are used to identify the allelic sequences present in a sample by determining which probes hybridize to the Glycophorin A sequences present in the sample. Suitable assay methods for detecting hybrids formed between probes and target nucleic acid sequences in a sample are known in the art (Sambrook et al., 1985, supra). Examples include the dot blot and reverse dot blot assay formats.

In a dot blot format, unlabeled amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

An alternate format is a "reverse" dot blot format, DNA is labeled and the target DNA is labeled and the probes are immobilized on a solid support, such as a nylon membrane. The target DNA is typically labeled during amplification by the incorporation of labeled primers. The membrane-probe complex is incubated with the labeled sample under suitable hybridization conditions, unhybridized sample is removed by washing under suitably stringent conditions, and the filter is then monitored for the presence of bound target DNA.

Alternatively, the reverse dot blot assay may be carried out using a solid support having a plurality of probe hybridization sites or wells. For example, a microwell plate is particularly useful in large scale clinical applications of the present methods. A reverse dot blot assay utilizing a microwell plate is described in copending U.S. patent application Ser. No. 695,072, filed May 3, 1991, which is a CIP of U.S. Ser. No. 414,542, filed Nov. 20, 1991, now abandoned, both incorporated herein by reference. Probes can be immobilized to a microwell plate either by passive binding or by first binding the probes to bovine serum albumen (BSA), which adheres to microwell plates.

Another suitable assay method system is described in U.S. Pat. No. 5,210,015, incorporated herein by reference, in which a labeled probe is added during the PCR amplification process. The probes are modified so as to prevent the probe from acting as a primer for DNA synthesis. Any probe which hybridizes to target DNA during each synthesis step is degraded by the 5' to 3' exonuclease activity of the DNA polymerase, e.g., Taq DNA polymerase. The degradation product from the probe is then detected. Thus, the presence of probe breakdown product indicates that hybridization between probe and target DNA occurred.

Whatever the method for determining which SSO probes of the invention hybridize to Glycophorin A allelic sequences in a sample, the central feature of the typing method involves the identification of the Glycophorin A alleles present in the sample by analyzing the pattern of binding of target DNA to a panel of SSO probes. The specific application will determine which probes are used in a panel. For instance, if only the presence or absence of the A' allele is of interest, a single probe specific for the A' allele is adequate.

DNA typing of Glycophorin A alleles is useful for many different purposes. For example, DNA typing methods now play a significant role in the important area of individual identification, whether for solving crimes, as when the identity of a criminal or victim is established by linking an individual with evidence left at the scene of a crime, or for solving other issues of a non-criminal nature, as when biological material is used to determine the maternity or paternity of an individual.

The typing methods of the present invention can be used to discover new alleles. New alleles have additional variation such that none of the sequence-specific probes are exactly complementary. Hence, a new allele will hybridize either more weakly or not at all to the set of probes used for typing. For example, the A' was first observed while screening polymerase chain reaction (PCR) amplified DNA containing the polymorphic region of the Glycophorin A for the A and B allele sequence variants with sequence-specific oligonucleotide probes. A significant fraction of the samples from African American individuals hybridized poorly to the A-specific probe, indicating an unknown allele containing additional sequence variation which inhibits hybridization. The existence of an additional allele was confirmed by direct sequencing of the PCR products from the above amplification.

The present invention also relates to kits, multicontainer units comprising useful components for practicing the present method. A useful kit can contain SSO probes for the Glycophorin A alleles. In some cases, the SSO probes may be fixed to an appropriate support membrane. The kit can also contain primers for PCR amplification, as such primers are useful in the preferred embodiment of the invention. These primers will amplify a polymorphic region of the Glycophorin A locus. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Glycophorin A Amplification and Typing

The typing of human genomic DNA samples with the panel of probes in the dot blot format is described below. The amplification and detection are carried out essentially as described in Saiki et al., 1988, Science 239:487–490, incorporated herein by reference.

Amplification

PCR amplifications are carried out in a total reaction volume of 100 μl containing 20 μl of DNA sample added to 80 μl of reaction mixture. The final reaction concentrations are as follows:

20 pmol RS362 (SEQ ID NO: 11)

20 pmol RS364 (SEQ ID NO: 12)

200 μM of each dNTP 70 mM KCl 14 mM Tris-HCl, pH 8.3

2.4 mM $MgCl_2$,

5 U Taq DNA polymerase (developed and manufactured by Hoffmann-La Roche and commercially available from Perkin Elmer, Norwalk, Conn.)

2 drops of mineral oil are added to the reaction to eliminate reagent evaporation.

Amplification reactions are carried out in a DNA Thermal Cycler 480, marketed by Perkin Elmer, Norwalk, Conn. The thermal cycler is programmed to provide 32 cycles (denature, anneal, and extend) followed by a final incubation (hold). Specific temperatures of each step are shown below.

| 32 cycles | denature | 60 seconds, 94° C. |
|---|---|---|
| | anneal | 30 seconds, 60° C. |
| | extend | 30 seconds, 72° C. |
| | hold | 7 minutes, 72° C. |

Reverse Dot Blot Format

In the reverse dot blot format, sequence-specific probes are immobilized on a membrane and amplified target DNA is hybridized to the membrane-bound probes as described in Saiki et al., 1989, Proc. Natl. Acad. Sci. 86:6230–6234, and in the AmpliType® HLA DQα DNA Typing Kit, developed and manufactured by Hoffmann-La Roche and marketed by Perkin Elmer, Norwalk, Conn., both incorporated herein by reference.

Amplification is carried out using biotinylated primers so as to incorporate a biotin label into the amplified product. The primers are biotinylated as described in Levenson and Chang, 1989, in PCR Protocols: A Guide to Methods and Applications (Innis et al., eds., Academic Press. San Diego) pages 92–112. Note that one or both of the primers can be biotinylated.

Detection is carried out by reacting streptavidin-conjugated horseradish peroxidase (SA-HRP) with any biotinylated, amplified DNA hybridized to the membrane-bound probe. The HRP thus becomes bound, through the SA-biotin interaction, to the amplified DNA and is used to generate a signal by the oxidation of tetramethylbenzidine (TMB) to form a blue precipitate (see U.S. Pat. No. 4,789, 630).

Although the probes can be fixed to the membrane by any means, a preferred method involves "tailing" the probe with a sequence of poly-dT. The resulting poly-dT "tail" can be reacted with amine groups on a nylon membrane to fix the probe covalently to the membrane. This reaction can be facilitated by UV irradiation. The probes provided in Table 2 contain 100 nucleotide poly-T tails.

Poly-dT tailed probes can be created either using terminal deoxyribonucleotidyl transferase (TdT, Ratlift Biochemicals; for the reactions below assume a concentration of about 120 Units/ml, which is 100 pmole/ml) or synthesized using a commercially available DNA synthesizer. If a DNA synthesizer is used to make the tailed probe, the tail should be synthesized on the 5' end of the probe, so that undesired premature chain termination occurs primarily in the tail region.

Poly-dT tails are added to probes using TDT as follows. TdT reactions are carried out in a 100 ml reaction containing 200 pmole of oligonucleotide probe, 800 μM dTT, 60 units of TdT, and 1× TdT salts (100 mM K-cacodylate, 1 mM $COCl_2$, 0.2 mM dithiothreitol, 25 mM Tris-Cl, pH 7.6, prepared as described by Roychoudhury and Wu, Meth. Enzymol. 65:43–62, incorporated herein by reference). The TdT reaction is carried out at 37° C. for two hours and then stopped by the addition of 100 μl of 10 mM EDTA, pH 8. The final concentration of tailed oligonucleotide is 1 μM (1 pmole/ml), and the length of the homopolymer tail is about 400 residues. Tail length can be changed by adjusting the molar ratio of dTTP to oligonucleotide. The tailed probes can be stored at −20° C. until use.

Two preferred nylon membrane strips for the reverse dot blot format are the Biodyne™ nylon membrane, 0.45 micron pore size (Pall, East Hills, N.Y.) and the Biotrans™ nylon membrane, 0.45 micron pore size, (ICN, Costa Mesa, Calif.). The probes can be spotted onto the strip conveniently with the Bio-Dot™ dot blot apparatus (Bio-Rad, Hercules, Calif.). Probes are spotted on discrete locations on the strip. About 2 to 10 picomoles of each tailed probe is premixed with 50–100 μl of TE buffer before application to the dot blot apparatus.

After dot blotting, the strip is briefly placed on absorbent paper to draw off excess liquid. The strip is then placed inside a UV light box, such as the Stratalinker™ light box (Stratagene, La Jolla, Calif.) and exposed to 50 to 60 millijoules/$cm^2$ of flux at 254 nm to fix the tailed probe to the nylon strip. After a brief rinse (about 15 minutes in hybridization solution) to remove unbound probe, the strip is ready for hybridization with biotinylated PCR product.

Hybridization reactions are carried out in an AmpliType® DNA typing tray (Perkin Elmer, Norwalk, Conn.). The probe-membrane strips are placed in the typing tray and 3 ml of hybridization solution (5× SSPE and 0.5% (w/v) SDS) are added to each probe strip. About 20 μl of PCR reaction mixture is added to each probe strip. Hybridization is carried out at 55° C. for 15 minutes in a rotating water bath.

After hybridization, the contents of each tray are aspirated and 5 ml of wash solution (2.5× SSPE and 0.1% (w/v) SDS) are added. The tray is agitated for several seconds to rinse the strips and the wash solution is aspirated.

An enzyme conjugate solution is prepared by adding 27 µl of enzyme conjugate (SA-HRP, available from Perkin Elmer, Norwalk, Conn.) to 3.3 ml of wash solution for each probe strip. Each probe strip is soaked in 3 ml of the enzyme conjugate solution and incubated at 55° C. for 5 minutes in a water bath. The enzyme conjugate is aspirated, the probe strips are rinsed with 5 ml of wash solution, and the wash solution is aspirated.

The stringent wash is carried out in 5 ml of wash solution at 55° C. for 12 minutes in a rotating water bath. After aspirating the wash solution, the probe strips are rinsed with 5 ml of wash solution, and the wash solution is aspirated.

Color development solution is prepared by mixing 5 ml of citrate buffer (0.1M Sodium Citrate, pH 5.0), 5 µl of 3% hydrogen peroxide, and 0.25 ml Chromogen:TMB Solution (Perkin Elmer, Norwalk, Conn.) for each probe strip. Each strip is soaked in 5 ml of citrate buffer, incubated at room temperature for 5 minutes on an orbital shaker (50 rpm), and the buffer is aspirated. Five ml of color development solution are added to each probe strip, and the strips are developed in the dark at room temperature for 20–30 minutes on an orbital shaker (50 rpm). The color development solution is aspirated and development is stopped by washing the strips in 5 ml glass-distilled water for 5 to 10 minutes in an orbital shaker (50 rpm). The wash step is repeated at least twice, preferably more.

The Glycophorin A type of the sample is determined from the pattern of probe hybridization which is visualized by the presence of blue dots. If a permanent record is desired, the probe strips should be photographed while still wet.

EXAMPLE 2

Frequencies of the Glycophorin A Alleles

To assess the frequency of the A' allele, samples from four different populations were typed at the Glycophorin A locus. The sampled populations consisted of 200 Caucasians, 100 Hispanics, 87 Japanese, and 300 African Americans, respectively. The amplification and reverse dot-blot detection were carried out essentially as described in Example 1. Allele frequency estimates for the three populations are given in Table II below. The A' allele was not distinguished from the A" allele, and the B allele was not distinguished from the B' allele.

TABLE III

| | Allele Frequency | | |
|---|---|---|---|
| Population | A | A', A" | B, B' |
| Caucasian | 0.52 | — | 0.48 |
| African American | 0.48 | 0.06 | 0.46 |
| Hispanic | 0.61 | — | 0.39 |
| Japanese | 0.52 | — | 0.48 |

EXAMPLE 3

AmpliType® PM Kit

In this embodiment, a Glycophorin A typing system is used in the AmpliType® PM PCR Amplification and Typing Kit developed and manufactured by Hoffmann-La Roche and marketed by Perkin Elmer, Norwalk, Conn. The AmpliType® PM kit contains DNA amplification reagents that direct the simultaneous amplification of specific regions of the following six genetic loci: Glycophorin A, HLA DQA1, Low Density Lipoprotein Receptor (LDLR), Hemoglobin G Gammaglobin (HBGG), D7S8, and Group Specific Component (GC). The AmpliType® PM kit also contains detection reagents and DNA probe strips for typing Glycophorin A, LDLR, HBGG, D7S8, and GC. Typing of these 5 loci is performed using the reverse dot blot format and colorimetric detection of hybridization duplexes as described above. If typing at the HLA DQA1 locus in desired, the AmpliType® PM +DQA1 Kit, developed and manufactured by Hoffmann-La Roche and marketed by Perkin Elmer, Norwalk, Conn., may be used which includes additional reagents for typing at the HLA DQA1 locus.

In a multi-allele typing system, it is desirable to design the system such that, at each locus, positive signals from each allele will produce signals of approximately equal intensity. The A, A', A", B, and B' Glycophorin A alleles are detected in the AmpliType® PM kit; however, the A, A', and A" allele are not discriminated, and the B and B' are not discriminated. A probe for the A and a probe for the A' and A" alleles are immobilized in the same dot on the nylon membrane in order to detect the A, A', and A" alleles with equal sensitivity. In this embodiment, the increased power of discrimination that could be achieved by detecting additional alleles at the Glycophorin A locus is not utilized.

The amplification protocol is as described in Example 1, above. Amplification reactions are carried out either in a DNA Thermal Cycler 480 or a GeneAmp PCR System 9600, both marketed by Perkin Elmer, Norwalk, Conn. If the DNA Thermal Cycler 480 is used, 2 drops of mineral oil are added to the reaction to eliminate reagent evaporation.

If the GeneAmp PCR System 9600 is used, the block is preheated to 95° C. prior to amplification. Using either thermal cycler, 32 amplification cycles (denature, anneal, and extend) are used followed by a final incubation (hold). Specific temperature profiles are shown below.

| | Thermal Cycler | |
|---|---|---|
| Step | 4800 | 9600 |
| denature | 60 seconds, 94° C. | 30 seconds, 95° C. |
| anneal | 30 seconds, 60° C. | 30 seconds, 63° C. |
| extend | 30 seconds, 72° C. | 30 seconds, 72° C. |
| hold | 7 minutes, 72° C. | 10 minutes, 72° C. |

In the AmpliType® PM kit, 6 loci are amplified and 5 loci are typed. The designation and sequence identification numbers of the primers and probes for all the loci used are listed below. The primers are biotinylated for use in the reverse dot blot detection assay. Only the hybridizing region of each probe is shown; each probe also contains a poly-T tail for immobilizing the probe to the nylon typing ship.

TABLE IV

Primer Pairs

| | Primer | Seq. ID No. | Sequence |
|---|---|---|---|
| Glycophorin A | RS362 | 11 | 5'-GGATGTGAGGAATTTGTCTTTTGCA |
| | RS364 | 12 | 5'-CCATTTGTCTGTGATGAGATGTAAC |
| HBGG | RS287 | 13 | 5'-GGCCAGTGACTAGTGCTGCAAGAA |
| | RS412 | 14 | 5'-AGACAATAAAGATGAACCCATAGTGAGC |
| LDLR | RR1000 | 15 | 5'-GCAGGAACGAGATCATCAGC |
| | RR1001 | 16 | 5'-TTCAGTGCCAACCGCCTCAC |
| DQA1 | RS134 | 17 | 5'-GTGCTGCAGGTGTAAACTTGTACCAG |
| | RS135 | 18 | 5'-CACGGATCCGGTAGCAGCGGTAGAGTTG |
| D7S8 | RS227 | 19 | 5'-CTAGGGATGTTCCTGTCTCAG |
| | RS383 | 20 | 5'-TGCCAAGCCCTGTTCTGCGA |
| GC | SN58 | 21 | 5'-CTGGCAGAGCGACTAAAAGCAAAATTG |
| | SN59 | 22 | 5'-ATCAATCTCTGAATCACAGTAAAGAGGAGG |

TABLE V

DNA Probe Strips

| Allele | Seq. ID No. | Sequence |
|---|---|---|
| Glycophorin A | | |
| A | 6 | 5'-CATTGCCACACCAGTGGTAC |
| A', A" | 7 | 5'-GTACCACTGAGGTGGCAATGATT |
| B, B' | 8 | 5'-CATTGCCACACCAGAGGTAC |
| HBGG | | |
| A | 23 | 5'-CACACCAAGCTTCCAC |
| B | 24 | 5'-ACACCCAGCTTCCACC |
| C | 25 | 5'-GGTGGAATCTTGGTGTG |
| LDLR | | |
| A | 26 | 5'-AGGATATGGTCCTCTTCCAC |
| B | 27 | 5'-GGGAGAGAACCATATCCTC |
| D7S8 | | |
| A | 28 | 5'-CCCGGAATGCTGG |
| B | 29 | 5'-CAGCATTCCAGGAAAGG |
| GC | | |
| (2) A | 30 | 5'-CCTTGGGGGTGGCATC |
| (1F) B | 31 | 5'-GATGCCATACCCACGGTT |
| (1S) C | 32 | 5'-GGCCGTGGGGGTGGCCTC |
| DQA1 | | |
| S | 33 | 5'-TTCTACGTGGACCTGGAGAGGAAGGAGACTGCCTG |

---

We claim:

1. A process for detecting the presence of an A', A", or B' allele of the Glycophorin A locus in a sample containing human nucleic acids comprising:

(a) mixing said nucleic acid with a sequence-specific oligonucleotide probe fully complementary to a variant sequence that distinguishes said allele from A and B alleles, under stringent hybridization conditions; and (b) detecting hybrids formed between said nucleic acid and said probe.

2. The process of claim 1, wherein said probe consists of a nucleotide sequence between 15 and 40 base pairs in length.

3. The process of claim 1, wherein said probe is SEQ ID NO: 8 or the complement of SEQ ID NO: 8.

4. The process of claim 1, wherein said nucleic acid is amplified prior to step (a).

5. The process of claim 4, wherein the amplification is achieved by a polymerase chain reaction using primers RS362, SEQ ID NO: 11, and RS364, SEQ ID NO: 12.

6. A process for determining an individual's Glycophorin A genotype from a sample containing nucleic acid obtained from said individual, said process comprising:

(a) mixing said nucleic acid with a panel of (SSO) probes, wherein said panel comprises a probe consisting of a nucleic acid sequence fully complementary to a variant sequence that distinguishes an A', A", or B' allele from A and B alleles, under stringent hybridization conditions; and (b) detecting hybrids formed between said nucleic acid and said SSO probes.

7. The process of claim 6, wherein said panel of probes comprises sequence-specific probes that distinguish A', A, and B alleles, wherein each of said probes consists of a nucleotide sequence between 15 and 40 nucleotides.

8. The process of claim 7, wherein said panel of SSO probes comprises a probe consisting of SEQ ID NO: 6 or the complement of SEQ ID NO: 6, a probe consisting of SEQ ID NO: 7 or the complement of SEQ ID NO: 7, and a probe consisting of SEQ ID NO: 8 or the complement of SEQ ID NO: 8.

9. The process of claim 6, wherein said nucleic acid is amplified prior to step (a).

10. The process of claim 9, wherein the amplification is achieved by a polymerase chain reaction using primers RS362, SEQ ID NO: 11, and RS364, SEQ ID NO: 12.

11. A purified sequence-specific oligonucleotide probe for detecting the presence of a variant sequence of a Glycophorin A locus, which distinguishes an A', A", or B' allele from A and B alleles, in a sample containing human nucleic acids, said probe consisting of a nucleotide sequence between 10 and 50 base pairs in length fully complementary to said variant sequence.

12. The probe of claim 11, wherein said nucleotide sequence is between 15 and 40 base pairs in length.

13. The probe of claim 12, wherein said nucleotide sequence is SEQ ID NO: 8 or the complement of SEQ ID NO: 8.

14. A panel of purified sequence-specific oligonucleotide probes useful for determining an individual's Glycophorin A genotype from a sample containing nucleic acid obtained from said individual, wherein said panel comprises a probe consisting of a nucleotide sequence fully complementary to a variant sequence that distinguishes an A', A", or B' from A and B alleles.

15. The panel of claim 14, wherein said probes are between 15 and 40 nucleotides in length.

16. The panel of claim 15, wherein said panel of SSO probes comprises a probe consisting of SEQ ID NO: 6 or the complement of SEQ ID NO: 6, a probe consisting of SEQ ID NO: 7 or the complement of SEQ ID NO: 7, and a probe consisting of SEQ ID NO: 8 or the complement of SEQ ID NO: 8.

17. A kit useful for determining the genotype of an individual at the Glycophorin A locus comprising the panel of claim 14.

18. The kit of claim 17, further comprising oligonucleotide primers useful for amplifying Glycophorin A nucleic acid.

19. A kit useful for determining the genotype of an individual at the Glycophorin A locus comprising the panel of claim 16.

20. The kit of claim 19, further comprising the primers RS362 (SEQ ID NO: 11), and RS364 (SEQ ID NO: 12).

21. A method for providing forensic evidence concerning the derivation of a human sample, wherein said method comprises:

(a) using the process of claim 6 to determine the genotype at the Glycophorin A locus of both said sample and a suspected individual, and (b) comparing the genotypes obtained.

\* \* \* \* \*

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATATGCTTTA TGGTCCGCTC AGTCACCTCG TTCTTAATCC CTTTCTCAAC TTCTATGTTA        60

TACAGCAATT GTGAGCATAT CAGCATCAAG TACCACTGGT GTGGCAATGC ACACTTCAAC       120

CTCTTCTTCA GTCACAAAGA                                                  140
```

(2) INFORMATION FOR SEQ ID NO:2:

(i) SEQUENCE CHARACTERISTICS:
           (A) LENGTH: 140 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:2:

```
ATATGCTTTA TGGTCTGCTC AGTCACCTCG TTCTTAATCC CTTTCTCAAC TTCTATTTTA        60

TACAGAAATT GTGAGCATAT CAGCATGGAG TACCTCTGGT GTGGCAATGC ACACTTCAAC       120

CTCCTCTTCG GTCACAAAGA                                                  140
```

(2) INFORMATION FOR SEQ ID NO:3:

(i) SEQUENCE CHARACTERISTICS:
           (A) LENGTH: 140 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:3:

```
ATATGCTTTA TGGTCTGCTC AGTCACCTCG TTCTTAATCC CTTTCTCAAC TTCTATTTTA        60

CACAGAAATT GTGAGCATAT CAGCATGGAG TACCTCTGGT GTGGCAATGC ACACTTCAAC       120

CTCCTCTTCG GTCACAAAGA                                                  140
```

(2) INFORMATION FOR SEQ ID NO:4:

(i) SEQUENCE CHARACTERISTICS:
           (A) LENGTH: 140 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:4:

```
ATATGCTTTA TGGTCCGCTC AGTCACCTCG TTCTTAATCC CTTTCTCAAC TTCTATTTTA        60

TACAGCAATT GTGAGCATAT CAGCATTAAG TACCACTGAG GTGGCAATGC ACACTTCAAC       120

CTCTTCTTCA GTCACAAAGA                                                  140
```

(2) INFORMATION FOR SEQ ID NO:5:

(i) SEQUENCE CHARACTERISTICS:
           (A) LENGTH: 140 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:5:

```
ATATGCTTTA TGGTCCGCTC AGTCACCTCG TTCTTAATCC CTTTCTCAAC TTCTATTTTA        60

TACAGAAATT GTGAGCATAT CAGCATTAAG TACCACTGAG GTGGCAATGC ACACTTCAAC       120
```

TTCTTCTTCA GTCACAAAGA 140

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CATTGCCACA CCAGTGGTAC 20

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTACCACTGA GGTGGCAATG ATT 23

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CATTGCCACA CCAGAGGTAC 20

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CTTCTATTTT ACACAGAAAT TGT 23

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTGAAGAAGA AGTTGAAGTG T 21

(2) INFORMATION FOR SEQ ID NO:11:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:11:

GGATGTGAGG AATTTGTCTT TTGCA                 25

( 2 ) INFORMATION FOR SEQ ID NO:12:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:12:

CCATTTGTCT GTGATGAGAT GTAAC                 25

( 2 ) INFORMATION FOR SEQ ID NO:13:

( i ) SEQUENCE CHARACTERISTICS:
   ( A ) LENGTH: 24 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:13:

GGCCAGTGAC TAGTGCTGCA AGAA                  24

( 2 ) INFORMATION FOR SEQ ID NO:14:

( i ) SEQUENCE CHARACTERISTICS:
   ( A ) LENGTH: 28 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:14:

AGACAATAAA GATGAACCCA TAGTGAGC               28

( 2 ) INFORMATION FOR SEQ ID NO:15:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:15:

GCAGGAACGA GATCATCAGC                    20

( 2 ) INFORMATION FOR SEQ ID NO:16:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:16:

TTCAGTGCCA ACCGCCTCAC    20

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GTGCTGCAGG TGTAAACTTG TACCAG    26

( 2 ) INFORMATION FOR SEQ ID NO:18:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CACGGATCCG GTAGCAGCGG TAGAGTTG    28

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CTAGGGATGT TCCTGTCTCA G    21

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TGCCAAGCCC TGTTCTGCGA    20

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CTGGCAGAGC GACTAAAAGC AAAATTG                                              27

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

ATCAATCTCT GAATCACAGT AAAGAGGAGG                                           30

( 2 ) INFORMATION FOR SEQ ID NO:23:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CACACCAAGC TTCCAC                                                          16

( 2 ) INFORMATION FOR SEQ ID NO:24:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

ACACCCAGCT TCCACC                                                          16

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GGTGGAATCT TGGTGTG                                                         17

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

AGGATATGGT CCTCTTCCAC                                                      20

( 2 ) INFORMATION FOR SEQ ID NO:27:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:27:

GGGAGAGAAC CATATCCTC 19

( 2 ) INFORMATION FOR SEQ ID NO:28:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

CCCGGAATGC TGG 13

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

CAGCATTCCA GGAAAGG 17

( 2 ) INFORMATION FOR SEQ ID NO:30:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

CCTTGGGGGT GGCATC 16

( 2 ) INFORMATION FOR SEQ ID NO:31:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

GATGCCATAC CCACGGTT 18

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:32:

GGCCGTGGGG GTGGCCTC                                                                                          1 8

(2) INFORMATION FOR SEQ ID NO:33:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:33:

TTCTACGTGG ACCTGGAGAG GAAGGAGACT GCCTG                                                                        3 5